US007674281B2

(12) United States Patent
Worm

(10) Patent No.: US 7,674,281 B2
(45) Date of Patent: Mar. 9, 2010

(54) APPARATUS AND METHODS FOR PROVIDING A FLOW OF A HEAT TRANSFER FLUID IN A MICROENVIRONMENT

(75) Inventor: Steve L. Worm, Raleigh, NC (US)

(73) Assignee: Forthright Engineering PLLC, Raleigh, NC (US)

( * ) Notice: Subject to any disclaimer, the term of this patent is extended or adjusted under 35 U.S.C. 154(b) by 1126 days.

(21) Appl. No.: 11/219,609

(22) Filed: Sep. 2, 2005

(65) Prior Publication Data

US 2007/0055325 A1 Mar. 8, 2007

(51) Int. Cl.
*A61F 7/12* (2006.01)
*A61F 7/00* (2006.01)
*F25D 23/12* (2006.01)
*A62B 17/00* (2006.01)

(52) U.S. Cl. ........................ 607/96; 607/104; 62/259.3; 128/201.29

(58) Field of Classification Search .................. 607/96; 62/259.3; 165/122
See application file for complete search history.

(56) References Cited

U.S. PATENT DOCUMENTS 2,347,984 A * 5/1944 Baskerville .................. 218/63
2,460,269 A 2/1949 Appeldoom
2,984,994 A 5/1961 Hankins
2,990,695 A 7/1961 Leffingwell, Jr.
3,000,191 A * 9/1961 Stark ........................... 62/291
3,064,448 A 11/1962 Whittington
3,108,575 A * 10/1963 Martinuzzi .................. 122/1 R
3,117,426 A 1/1964 Rischer et al.
3,161,192 A 12/1964 McCormack
3,248,897 A 5/1966 Stark
3,343,536 A * 9/1967 Brisson et al. ......... 128/202.11
3,526,102 A 9/1970 Boylett et al.
3,558,852 A * 1/1971 Larenzo et al. ............. 219/211
3,666,007 A * 5/1972 Yoshino et al. ............... 96/144
3,815,573 A * 6/1974 Marcus ....................... 126/204
3,869,871 A * 3/1975 Rybalko et al. ............... 62/178
4,172,454 A * 10/1979 Warncke et al. ........ 128/201.29
4,738,119 A 4/1988 Zafred (Continued)

OTHER PUBLICATIONS

International Search Report and the Written Opinion of the International Searching Authority for PCT Application No. PCT/US2006/33404, mailed Apr. 30, 2007.

*Primary Examiner*—Roy D Gibson
*Assistant Examiner*—Kaitlyn E Helling
(74) *Attorney, Agent, or Firm*—Myers Bigel Sibley & Sajovec, P.A.

(57) ABSTRACT

A microenvironment system for use with a heat transfer fluid includes a microenvironment structure and a fluid handling apparatus. The microenvironment structure defines a flow passage to receive a flow of the heat transfer fluid therethrough. The fluid handling apparatus is adapted to provide a flow of the heat transfer fluid through the flow passage. The fluid handling apparatus includes a gas driven pump and a supply of a phase change material (PCM). The gas driven pump is operable to force the flow of the heat transfer fluid through the flow passage. The supply of the PCM is convertible from a solid and/or liquid phase to a gas phase to provide a pressurized drive gas. The fluid handling apparatus is configured to drive the gas driven pump using the pressurized drive gas from the supply of the PCM.

14 Claims, 3 Drawing Sheets

U.S. PATENT DOCUMENTS

| | | | | |
|---|---|---|---|---|
| 4,998,415 | A | | 3/1991 | Larsen |
| 5,092,129 | A | | 3/1992 | Bayes et al. |
| 5,115,859 | A | * | 5/1992 | Roebelen et al. .............. 165/10 |
| 5,197,294 | A | | 3/1993 | Galvan et al. |
| 5,214,926 | A | | 6/1993 | Mandin et al. |
| 5,333,677 | A | * | 8/1994 | Molivadas .................. 165/272 |
| 5,361,591 | A | * | 11/1994 | Caldwell .................... 62/50.4 |
| 5,415,222 | A | | 5/1995 | Colvin et al. |
| 5,438,707 | A | | 8/1995 | Horn |
| 5,689,968 | A | | 11/1997 | Frustaci et al. |
| 5,709,203 | A | | 1/1998 | Gier |
| 5,837,002 | A | | 11/1998 | Augustine et al. |
| 6,105,382 | A | | 8/2000 | Reason |
| 6,550,471 | B2 | | 4/2003 | Szymocha et al. |
| 6,858,068 | B2 | | 2/2005 | Smith et al. |
| 6,901,608 | B2 | | 6/2005 | Szczesuil et al. |
| 6,915,641 | B2 | | 7/2005 | Harvie |

* cited by examiner

APPARATUS AND METHODS FOR PROVIDING A FLOW OF A HEAT TRANSFER FLUID IN A MICROENVIRONMENT

FIELD OF THE INVENTION

The present invention relates to apparatus and methods for handling a heat transfer fluid in a microenvironment.

BACKGROUND OF THE INVENTION

It is often desirable or necessary to provide supplemental cooling to microenvironments or microclimates such as personal microenvironments. A personal microenvironment is an environment that exists in close proximity to an individual and moves with the individual as the individual moves. Examples of personal microenvironments include hazardous material (hazmat) suits, chemical/biological personal protective equipment, body armor, bombproof suits, turnout gear (e.g., fireman's gear), other protective gear worn by emergency responders and the like, etc. Such gear may tend to trap heat (including body heat) and humidity (e.g., from perspiration) within the gear. The trapped heat and humidity may cause the wearer discomfort. Under strenuous conditions and/or when there is a high ambient temperature, the wearer may suffer from heat exhaustion, resulting in reduced performance and potentially life threatening injury.

SUMMARY OF THE INVENTION

According to embodiments of the present invention, a microenvironment system for use with a heat transfer fluid includes a microenvironment structure and a fluid handling apparatus. The microenvironment structure defines a flow passage to receive a flow of the heat transfer fluid therethrough. The fluid handling apparatus is adapted to provide a flow of the heat transfer fluid through the flow passage. The fluid handling apparatus includes a gas driven pump and a supply of a phase change material (PCM). The gas driven pump is operable to force the flow of the heat transfer fluid through the flow passage. The supply of the PCM is convertible from a solid and/or liquid phase to a gas phase to provide a pressurized drive gas. The fluid handling apparatus is configured to drive the gas driven pump using the pressurized drive gas from the supply of the PCM.

According to further embodiments of the present invention, a fluid handling apparatus for providing a flow of a heat transfer fluid through a flow passage of a microenvironment structure includes a gas driven pump and a supply of a phase change material (PCM). The gas driven pump is operable to force the flow of the heat transfer fluid through the flow passage. The supply of the PCM is convertible from a solid and/or liquid phase to a gas phase to provide a pressurized drive gas. The fluid handling apparatus is configured to drive the gas driven pump using the pressurized drive gas from the supply of the PCM.

According to further embodiments of the present invention, a method for providing a flow of a heat transfer fluid through a flow passage of a microenvironment structure includes: providing a supply of a phase change material (PCM) in a solid and/or liquid phase; converting the supply of the PCM from the solid and/or liquid phase to a gas phase to generate a pressurized drive gas; and driving a gas driven pump using the pressurized drive gas from the supply of the PCM such that the gas driven pump forces the flow of the heat transfer fluid through the flow passage.

According to further embodiments of the present invention, a microenvironment system for use with a heat transfer fluid includes a microenvironment structure and a fluid handling apparatus. The microenvironment structure defines a flow passage to receive a flow of the heat transfer fluid therethrough. The fluid handling apparatus is adapted to provide the flow of the heat transfer fluid through the flow passage. The fluid handling apparatus includes a heat exchanger, a supply of a phase change material (PCM) convertible from a solid and/or liquid phase to a gas phase to provide a flow of a cooling gas through the heat exchanger, and a pump. The pump is operable to force the flow of the heat transfer fluid through the flow passage and across the heat exchanger such that heat from the flow of the heat transfer fluid is transferred to the cooling gas via the heat exchanger. The fluid handling apparatus is adapted to discharge the cooling gas after the cooling gas flows through the heat exchanger.

Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF THE PREFERRED EMBODIMENTS

Figure 1:
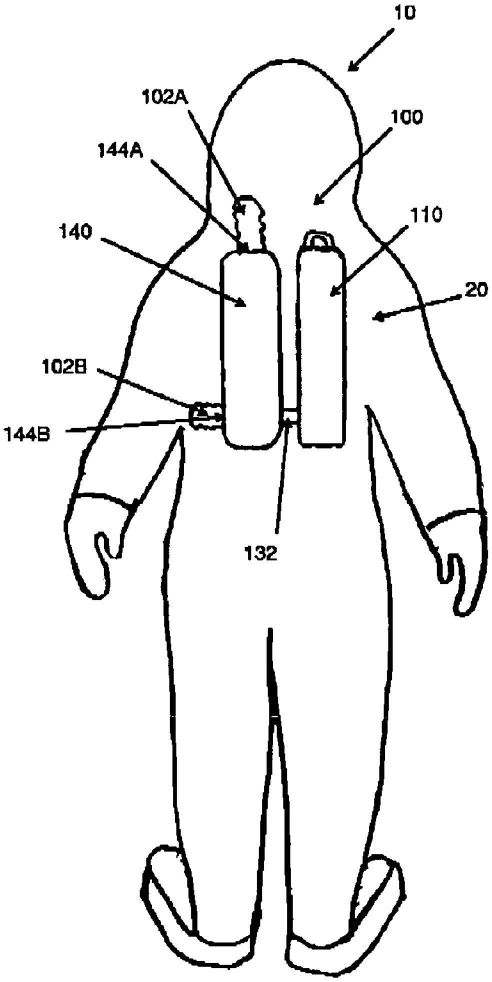
FIG. 1 is a rear view of a personal microenvironment system according to embodiments of the present invention.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout. As used herein the term "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In accordance with embodiments of the present invention, apparatus and methods are provided for generating a flow of a heat transfer fluid ("HTF") in a microenvironment. The apparatus and methods of the invention employ a phase change material ("PCM") to drive a gas driven pump, which in turn generates the flow of heat transfer fluid. According to some embodiments, the apparatus and methods further serve to condition the heat transfer fluid by removing humidity from the heat transfer fluid. In particular, the apparatus and methods may be used to cool the heat transfer fluid and direct the cooled heat transfer fluid into the microenvironment. According to some embodiments, the PCM is carbon dioxide ($CO_2$). According to some embodiments, the heat transfer fluid is air. Further aspects and benefits of the apparatus and methods of the present invention will be apparent from the description that follows.

According to some embodiments, the microenvironment is a personal microenvironment or microclimate. As used herein, a "personal microenvironment" means an environment that exists in close proximity to an individual and moves with the individual as the individual moves. Examples of personal microenvironments include garments such as hazardous material (hazmat) suits, chemical/biological personal protective equipment, body armor, bombproof suits, turnout gear (e.g., fireman's gear), other protective gear worn by emergency responders and the like, etc.

Figure 2:
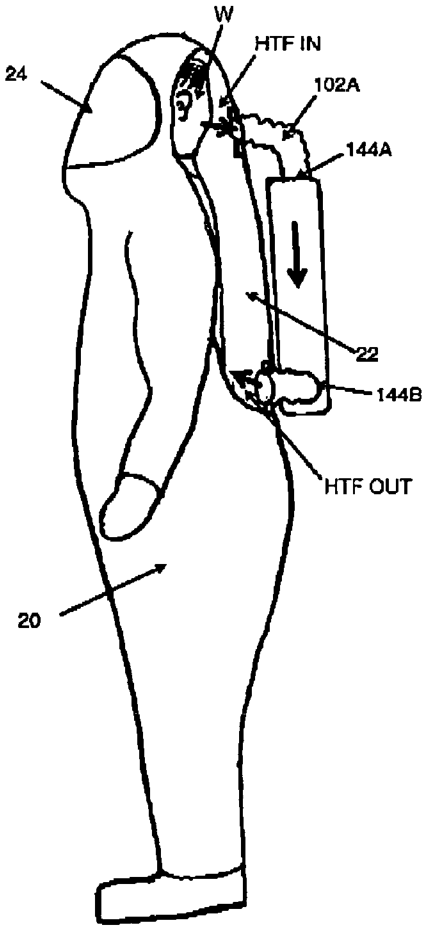
FIG. 2 is a side view of the personal microenvironment system of FIG. 1.
Figure 3:
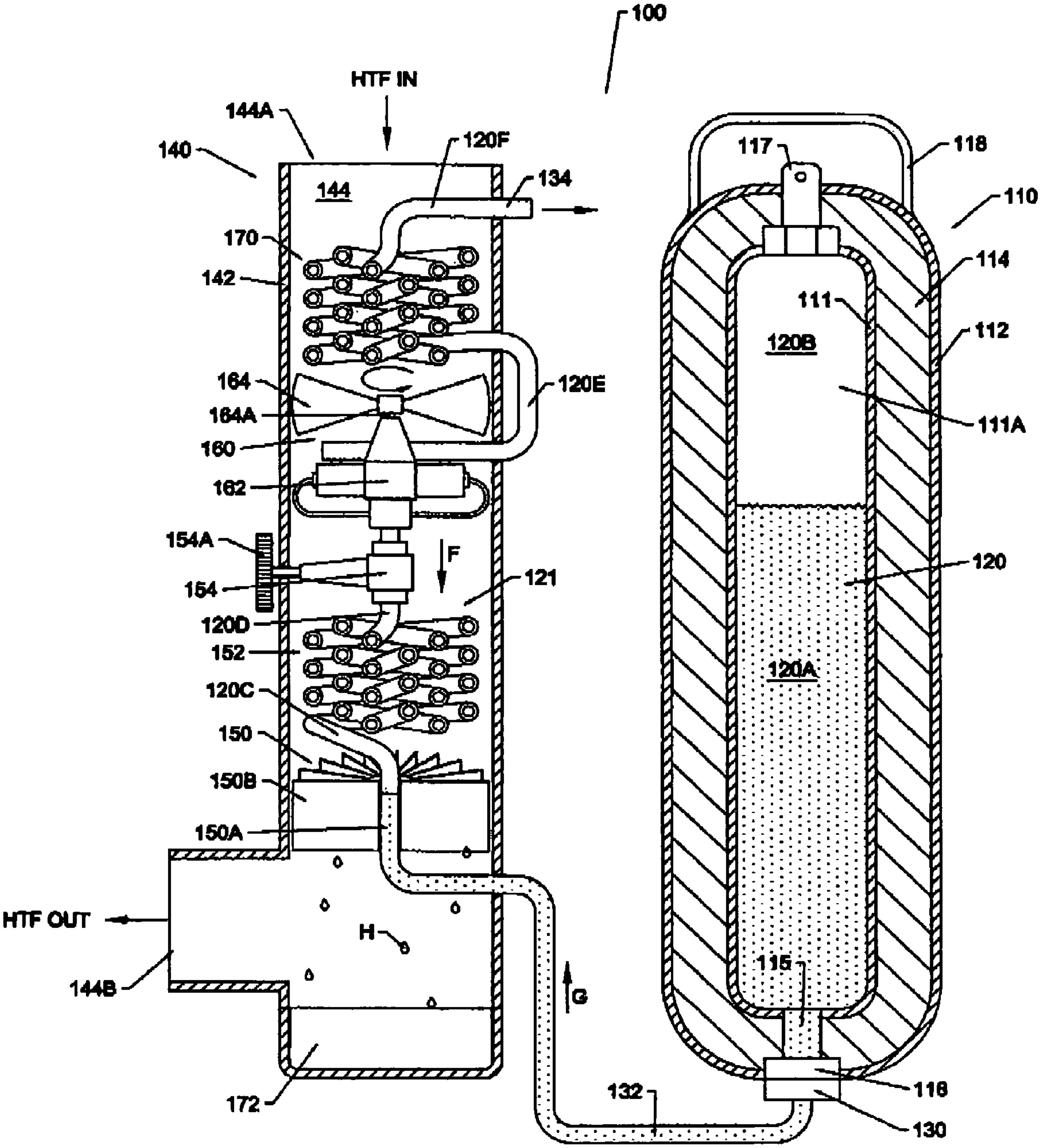
FIG. 3 is an enlarged, fragmentary, cross-sectional view of a fluid handling apparatus forming a part of the personal microenvironment system of FIG. 1 in accordance with embodiments of the present invention.

With reference to FIGS. 1-3, a personal microenvironment system 10 according to embodiments of the present invention is shown therein. The personal microenvironment system 10 includes a suit 20 and a fluid handling apparatus 100. Generally, the suit 20 provides a personal microenvironment and the fluid handling apparatus 100 serves to generate a flow of a heat transfer fluid (HTF) through the suit 20. The fluid handling apparatus 100 may also dehumidify and/or cool the heat transfer fluid before introducing the heat transfer fluid into the suit 20.

Referring to FIGS. 1 and 2, the suit 20 is adapted to be worn by a user or wearer W and defines an interior chamber 22 (FIG. 2). As illustrated, the suit 20 includes a transparent mask 24. The suit 20 may be, for example, a hazardous material suit. As such, the system 10 may be a sealed, closed loop system so that air is not exchanged between the interior and the exterior of the suit 20 in use. Suitable materials, constructions and modifications for the suit 20 are known to those of skill in the art and will not be discussed in detail herein.

The fluid handling apparatus 100 is operably connected to the suit 20 and may be integral with or detachably mounted on the suit 20. As illustrated, the fluid handling apparatus 100 is mounted on the outside of the suit 20. However, according to some embodiments, the fluid handling apparatus may be contained wholly or partly within the suit 20.

The fluid handling apparatus 100 includes a storage vessel assembly 110 and a heat transfer fluid (HTF) handler assembly 140. As shown in FIG. 3, the storage vessel assembly 110 contains a supply of a phase change material (PCM) 120. The HTF handler assembly 140 includes a PCM handler subassembly 121 including a network of components and piping as discussed in more detail below.

The PCM handler subassembly 121 operates to generate a flow of the heat transfer fluid. More particularly, heat transfer fluid (HTF IN) is drawn by the PCM handler subassembly 121 from the chamber 22 of the suit 20 through an intake conduit 102A and into the HTF handler assembly 140. The PCM handler subassembly 121 forces the heat transfer fluid through the HTF handler assembly 140 (generally, in a flow direction F) and then back into the chamber 22 through a distribution conduit 102B (HTF OUT). The heat transfer fluid flows through the flow passage defined by the suit 20 within the chamber 22 and back to the conduit 102A. As the heat transfer fluid is passed through the HTF handler assembly 140, the heat transfer fluid is cooled and dehumidified by the HTF handler assembly 140. More particularly, the heat transfer fluid is forced across one or more heat exchanger surfaces where heat is transferred from the heat transfer fluid to the PCM. The heat transfer fluid may be recirculated in this manner to continually cool and dehumidify the chamber 22 in which the wearer W is situated. In the illustrated embodiment, the PCM 120 flows through the PCM handler subassembly 121 generally in a flow direction G that is counter to the heat transfer fluid flow direction F. The inlet 144A and/or the outlet 144B may be connected to the chamber 22 at more than one location.

Turning to the fluid handling apparatus 100 in more detail, the PCM 120 is a pure substance or compound that is able to make a distinct transition from either a liquid phase or solid phase into a gas phase at a specific temperature, and takes in large amounts of energy in the process. The liquid or solid phases of a material or compound at a particular temperature and pressure are necessarily at a lower energy state than the gas phase of that same material or compound at the same pressure and temperature. Therefore the transition from a liquid or solid phase to a gas phase requires the input of heat energy, or said another way, the phase change material adsorbs heat when it changes phase. The PCM 120 may be supplied in a liquid or solid phase. According to some embodiments, the PCM, at standard conditions, has a vapor pressure at ambient temperature that is greater than atmospheric pressure. According to some embodiments, the PCM 120 is $CO_2$. However, other PCMs may be used. Examples of other PCMs that could be used include ammonia, nitrogen, oxygen, helium, HFC's, CFC's, and/or mixtures thereof. Carbon dioxide has the advantages that it is environmentally benign, has relatively low toxicity, is inexpensive, and has a relatively low vapor pressure. Carbon dioxide is very widely produced and utilized throughout the world as a means of carbonating beverages such as soft drinks and beer. For this reason, the methods of producing, storing and distributing carbon dioxide are well developed and widely available. The PCM 120 will be referred to hereinafter as $CO_2$, it being appreciated that, in accordance with other embodiments, other phase change materials may be used in place of or in addition to the $CO_2$, with or without suitable modifications the apparatus and methods described.

The storage vessel assembly 110 includes an inner vessel 111 defining a chamber 111A within which the $CO_2$ 120 is stored until it is used by the fluid handling apparatus 100. According to some embodiments, and as illustrated, the $CO_2$ 120 within the chamber 111A is saturated and includes liquid phase $CO_2$ 120A. Gas phase $CO_2$ 120B may also be present in the chamber 110A. The inner vessel 111 should have sufficient strength to withstand the pressure of the saturated $CO_2$. The inner vessel 111 may be formed of high strength aluminum alloy, aluminum, stainless or carbon steel or an alloy thereof, carbon fiber/epoxy composite, carbon fiber/epoxy/Kevlar composite, and/or titanium.

Thermal insulation 114 surrounds the inner vessel 111 and may serve to reduce the rate of heat transfer from the environment to the $CO_2$ 120 in the inner vessel 111. The thermal insulation 114 may include an evacuated space, foam, mineral wool, fiberglass, etc. The thermal insulation 114 may serve to reduce the rate of heat transfer from the environment to the $CO_2$ stored in the vessel 111. The temperature of the liquefied $CO_2$ 120 in the inner vessel 111 may be significantly below ambient temperature. Heat transfer from the environment to the stored liquid $CO_2$ may cause the liquid $CO_2$ to change phase to gaseous $CO_2$, thereby reducing the amount of cooling that the fluid handling apparatus 100 can provide for a given size storage vessel 111. The thermal insulation may also provide a moisture barrier in order to prevent condensation of ambient moisture onto the storage vessel assembly 110.

A protective shell 112 may surround and protect the storage vessel 111 from inadvertent puncture due to an accidental collision, ballistics, etc. The protective shell 112 may also serve to control the sudden release of energy that could result from a puncture of the storage vessel 111. The protective shell 112 can be fabricated from Kevlar, form steel, carbon fiber/epoxy composite, aluminum, etc.

A carry handle 118 may be provided on the $CO_2$ storage vessel assembly 110 to assist in the removal and replacement of the storage vessel assembly 110.

A bleed or relief valve 117 is provided at the top of the storage vessel 111 and fluidly communicates with the chamber 111A. The valve 117 is located above the gas space of the chamber 111A. The valve 117 allows $CO_2$ vapor 120B to escape in a controlled manner from the chamber 111A as necessary to maintain the pressure (and temperature) of the contained $CO_2$ at a predetermined level. Also, the valve 117 protects the storage vessel 111 from overpressure in the event that it is accidentally exposed directly to fire or to another source of excessive heat.

An outlet opening 115 fluidly connects the chamber 111A with a feed conduit 132. Cooperating quick disconnect fittings 116 and 130 are secured to the storage vessel assembly 110 and the conduit 132, respectively, to allow for the safe and rapid removal and replacement of the storage vessel assembly 110 on the fluid handling apparatus 100. One or both of the fittings 116, 130 may include an automatic shutoff feature to ensure that the flow of $CO_2$ from the storage vessel is stopped whenever the storage vessel assembly 110 is disconnected from the rest of the fluid handling apparatus 100. A restricting orifice (not shown) may also be provided in the inlet 115 or elsewhere to restrict the maximum possible flow of the liquid $CO_2$ 120A from the storage vessel 111 in the event of a failure of downstream components. In this event, the restricting orifice restricts the maximum flow of liquid $CO_2$ from the storage vessel 111 to a safe rate.

The HTF handler assembly 140 includes a tubular housing 142. The housing 142 defines a flow passage or plenum 144 having an inlet 144A and an outlet 144B. The inlet 144A is fluidly connected to the intake conduit 102A. The outlet 144B is fluidly connected to the distribution conduit 102B. The housing 142 may be formed of any suitable material such as, for example, polycarbonate and/or aluminum.

An evaporator 150 is disposed in the housing 140 in the passage 144 and is fluidly connected to the vessel 111 via the conduit 132. The evaporator 150 serves as a heat exchanger that transfers heat from the heat transfer fluid stream to the $CO_2$ in the evaporator 150 to vaporize the $CO_2$ from a liquid state to a gas state. According to some embodiments, most of the heat that is transferred between the heat transfer fluid stream and the $CO_2$ within the apparatus 100 occurs in the evaporator 150. The evaporator 150 can be fabricated from a short length of tubing 150A that is in intimate contact with extended surface area such as a plurality of fins 150B. Heat is transferred from the heat transfer fluid stream to the evaporator fins 150B and then to the tubing 150A where it boils the $CO_2$ liquid 120A to make $CO_2$ vapor 120C which will be at approximately the same pressure and temperature as the $CO_2$ liquid upstream in the conduit 132 and the storage vessel 111.

The tubing 150A may be fabricated of stainless steel, carbon steel, aluminum alloy or copper having an inner diameter of approximately ⅛" and an outer diameter of about ¼" and a length of about 1". There may be between 5 and 50 fins 150B located on the outside of the tubing. According to some embodiments, the fins 150B are approximately 0.5" high, 1" long and 0.10" thick. The fins 150B can be fabricated by extrusion, stamping, machining or other means and then bonded to the tube 150A by welding, brazing, gluing, or mechanical fastening. The fins 150B can be made from aluminum, copper or other metal having a high thermal conductivity.

A superheater 152 is mounted in the housing 140 in the passage 144 and is fluidly connected to the evaporator 150 via the conduit 132. The superheater 152 serves as a heat exchanger that transfers heat from the heat transfer fluid stream to the $CO_2$ gas within the superheater 152. The superheater 152 may serve to warm the relatively cold $CO_2$ leaving the evaporator 150 before the $CO_2$ gas is introduced into a gas driven motor 162 as discussed below. Warming of the $CO_2$ gas before it enters the motor 162 may be desirable or necessary in order to insure that as the $CO_2$ gas passes through the motor 162 it does not recondense to form liquid or solid $CO_2$ which could damage the motor 162 and/or reduce its performance. The superheater 152 may also remove some heat from the heat transfer fluid stream.

The superheater 152 can be fabricated from a length of tubing having an inner diameter of approximately ⅛" and an outer diameter of about ¼" and a length of at least six inches. The superheater tube may also have fins on the external and/or internal surfaces. The tube may be formed into a compact configuration so that it can fit into the passage 144 without overly obstructing the flow of the heat transfer fluid therethrough. The tube could be formed, for example, into a helical configuration having several layers in the radial and axial directions. According to some embodiments, the "evaporator" and "superheater" functions as described herein can be performed by a single part (e.g., a finned tube) providing both of these functions.

The general "shell and tube" HTF/working fluid heat exchanger arrangement described herein could be also be of the "compact heat exchanger" type also called "plate and frame" such as are produced by Alpha Laval or, alternatively, could be of the annular "tube in tube" arrangement. The compact or tube in tube arrangements may be preferable when the heat transfer fluid is a liquid (such as glycol) rather than a gas (such as air).

A metering valve 154 is located between the superheater 152 and the motor 162. The metering valve 154 can be used to selectively regulate the flow of gaseous $CO_2$ through the HTF handler assembly 140 and thereby control the overall rates of heat transfer fluid flow and heat removal provided by the apparatus 100. The metering valve 154 may be of any suitable construction. Suitable valves may include a needle valve, a gate valve or a globe valve. The metering valve 154 may be manually and/or automatically adjusted. As illustrated, the metering valve 154 is provided with a control knob 154A to open and close the metering valve 154. Alternatively or additionally, the metering valve 154 could, for example, be connected via a mechanism to a bimetallic strip which is located within or in close proximity to the microclimate to serve as a thermostatic controller (not shown).

The HTF handler assembly 140 further includes a gas driven pump 160. The gas driven pump 160 includes the gas driven motor 162 and fan blades 164. The pressurized $CO_2$ vapor that is generated in the evaporator 150 and warmed in the superheater 152 is directed to the motor 162 where it is used to turn a shaft 164A connected to the fan blades 164A. Any suitable gas driven motor may be used. According to some embodiments, the motor 162 is a reciprocating piston type motor (e.g., as sold by Gasparin, Inc. of the Czech Republic). According to some embodiments, the motor 162 is turbine type motor such as are commonly used in air dental drills and air grinders. According to some embodiments, the motor 162 is located inside of the housing 142 and the flow passage 144 as shown, but the motor 162 could be located outside of the housing 142 and the flow passage 144. A pressure relief valve (not shown) may be located upstream (relative to the $CO_2$ flow path) of the motor 162 to prevent overpressure of the motor 162. A silencer or muffler (not shown) may be provided on the exhaust of the motor 162 in order to reduce audible noise generated by the motor 162. The silencer could be of a shell and baffle configuration or could be a length of tubing.

A scavenger 170 is located downstream (relative to the $CO_2$ flow path G) of the motor 162 and positioned in the flow passage 144. The scavenger 170 is a heat exchanger and may be constructed as described above with regard to the superheater 152. Following the scavenger 170, the $CO_2$ is discharged from the HTF handler assembly 140 through an exhaust conduit 134. The scavenger 170 may serve to exchange additional heat from the conditioned heat transfer fluid stream to the $CO_2$ before the $CO_2$ is discharged. The scavenger 170 may also serve to quiet the audible noise generated by the motor 162.

The $CO_2$ may be directed from the exhaust conduit 134 into the external (i.e., ambient) environment, into the conditioned heat transfer fluid stream, and/or into a low pressure receptacle. Discharging the $CO_2$ into the conditioned heat transfer fluid stream may provide an additional cooling effect. In this case, it may be preferable to omit the scavenger 170.

An absorbent pad 172 is located at the bottom end of the housing 142. The pad 172 serves to collect moisture that has condensed onto the outside of the evaporator 150 and/or other heat exchange surfaces for later removal from the housing 142 (e.g., through an access cover). The condensed moisture may be delivered to the pad 172 via gravity as illustrated. The pad 172 can be fabricated from cellulose material such as is used in diapers, zeolite, silica gel and/or other adsorbent materials, for example. Other structures for collecting or draining the condensed moisture may be provided in addition to or in place of the pad 172.

The operation of the system 10 and the fluid handling apparatus 100 will now be described in more detail. It will be appreciated that various of the operations, steps and parameters mentioned hereinbelow may be omitted or modified in accordance with other embodiments of the invention.

The liquid $CO_2$ 120A is stored in the storage vessel 111. According to some embodiments, the liquid $CO_2$ 120A is stored at a pressure of between about 100 and 800 psia and, according to some embodiments, between about 140 and 160 psia. According to some embodiments, the liquid $CO_2$ 120A is stored at a temperature of between about −58 and 65° F. and, according to some embodiments, between about −42 and −35° F. The bleed valve 117 at the top of the storage vessel 111 allows gaseous $CO_2$ 120B to escape from the storage vessel as necessary to keep the pressure within the storage vessel at the desired level. When the metering valve 154 is opened, the liquid $CO_2$ 120A passes from the bottom of the storage vessel 111, through the outlet 115, and then through the conduit 132 to the evaporator 150.

Within the evaporator 150, latent and sensible heat are transferred from the heat transfer fluid stream which is to be conditioned to the liquid $CO_2$ 120A where it causes the liquid $CO_2$ to change to $CO_2$ vapor 120C. The $CO_2$ vapor 120C leaving the evaporator 150 may have substantially the same temperature and pressure as the liquid $CO_2$ 120A entering the evaporator 150.

After the $CO_2$ vapor 120C passes from the evaporator 150, the relatively cold $CO_2$ gas 120C passes through the superheater 152 where additional heat is transferred to it from the conditioned heat transfer fluid stream so that the temperature of the $CO_2$ gas 120C is raised. According to some embodiments, the temperature of the $CO_2$ gas is raised to between about 40 and 80° F. and, according to some embodiments, to between about 55 and 65° F. According to some embodiments, although the temperature of the $CO_2$ gas is raised as just described, the pressure of the superheated $CO_2$ gas 120D is substantially the same as the pressure of the $CO_2$ gas 120C. According to some embodiments, the $CO_2$ gas is superheated by the superheater 152 such that its temperature exiting the superheater 152 is greater than its saturation temperature for its pressure at the exit of the superheater 152. According to some embodiments, the $CO_2$ gas is superheated by at least about 75° F. at the exit of the superheater 152.

After leaving the superheater 152, the superheated $CO_2$ gas 120D flows through the metering valve 154 which is adjusted to regulate the rate of $CO_2$ flow to the motor 162.

After the metering valve 154, the $CO_2$ gas 120D (which may be superheated as discussed above) flows through the gas driven motor 162 of the gas driven pump 160, which extracts work from the $CO_2$ gas 120D in order to rotate the fan blades 164. This is accomplished, for example, in the case of a reciprocating $CO_2$ motor by the pressure of the $CO_2$ gas alternately pushing against one or more pistons contained within one or more cylinders. The pistons are connected to and rotate a crankshaft which in turn rotates the shaft 164A. The forced rotation of the fan blades 164A by the motor 162 induces the heat transfer fluid to flow through the inlet 144A (from the intake conduit 102A), through the passage 144, and through the outlet 144B (to the distribution conduit 102B) in the flow direction F, thereby generating the heat transfer fluid stream or flow across the heat exchange surfaces of the PCM handler subassembly 121.

As the $CO_2$ gas passes through the motor 162 and work energy is extracted from it, the temperature and pressure of the $CO_2$ gas are reduced so that the $CO_2$ gas 120E exiting the motor 162 has a much lower temperature and a much lower pressure than the gas 120D entering at the motor inlet. According to some embodiments, the temperature of the $CO_2$ gas 120E is between about −20 and 20° F. and the pressure of the $CO_2$ gas 120E is between about 15 and 25 psia. According to some embodiments, the $CO_2$ remains superheated as it passes through the motor 162 at least to the exit of the motor 162. According to some embodiments, the $CO_2$ gas is superheated by at least 60° F. at the exit of the motor 162.

The $CO_2$ gas 120E then passes through the scavenger 170 in order to allow additional heat to be transferred from the heat transfer fluid stream to the $CO_2$ gas 120E. The warmed $CO_2$ gas 120F is then vented or discharged through the conduit 134 into the external ambient environment, into the heat transfer fluid stream, or elsewhere as desired. Thus, in accordance with embodiments of the invention, the $CO_2$ is provided in bulk, circulated through the PCM handler subassembly 121, and vented rather than being recycled or re-used in a closed loop PCM circuit.

The heat transfer fluid stream (e.g., air stream) may contain significant levels of water vapor. Moisture will therefore condense onto the external heat exchanger surfaces and will fall by gravity to the bottom of the housing 142 where it will be collected. This moisture can be retained by the adsorbent pad 172 until a time when it is convenient to physically remove the pad 172 and the retained liquid from the housing 142.

Thus, in view of the foregoing description, it will be appreciated that the fluid handling apparatus 100 can provide both a forced flow of the heat transfer fluid through the suit 20 and conditioning of the heat transfer fluid. Such conditioning may include cooling of the heat transfer fluid and/or dehumidification of the heat transfer fluid. In particular, the fluid handling apparatus 100 may provide both cooling and dehumidification of the heat transfer fluid to effectively remove heat and moisture (e.g., from perspiration) from the chamber 22 of the suit 20. That is, relatively warm, moist air flows from the personal microenvironment to the HTF handler assembly 140 where it is conditioned and returned to the personal microenvironment at a lower temperature and lower moisture content.

According to some embodiments, the heat transfer fluid is air and the temperature of the air is reduced by between about 5 and 110° F. between the inlet 144A and the outlet 144B. According to some embodiments, the heat transfer fluid is air and the dew point of the air is reduced by between about 1 and 6° F. between the inlet 144A and the outlet 144B.

The apparatus and methods in accordance with the present invention may provide a number of advantages. The fluid handling apparatus may be relatively light weight, compact, rugged, reliable, inexpensive, quiet to operate and easy to maintain. The devices can be fabricated from commonly available materials and components and can therefore be manufactured at relatively low cost in comparison to alternative technologies. In addition to removing sensible heat from a personal or other microenvironment, the device can be capable of removing the latent heat associated with water vapor contained within air or other heat transfer fluid of the microenvironment. This may be particularly beneficial in the case of a personal microenvironment because perspiration within the personal microenvironment can quickly lead to high relative humidity within the personal microenvironment, which can greatly inhibit the cooling effectiveness of perspiring.

The heat transfer fluid may be a gas or a liquid. According to some embodiments, the heat transfer fluid is air. According to some embodiments, the heat transfer fluid is liquid glycol (e.g., ethylene glycol or propylene glycol).

While the PCM flow (e.g., the $CO_2$ flow) and the heat transfer fluid flow in the passage 144 are described hereinabove as being in generally opposite directions, it is also contemplated that the two flows may be in substantially the same direction.

While a gas driven pump 160 including a gas driven motor 162 and fan blades 164 has been described herein, gas driven pumps of other types and configurations may be employed. As illustrated in FIG. 3, the fan blade 164 is of the axial type, but could also be of the radial type such as are referred to as a blower (when the fluid is a gas) or an impeller (when the fluid is a liquid). As a further alternative, the fluid moving pump could be of the positive displacement type, which may be referred to as a piston pump.

While the illustrated system 10 includes a closed loop personal microenvironment, in accordance with other embodiments of the present invention an open loop system is provided in which ambient air is passed through the fluid handling apparatus (where it may be conditioned as described above) and then into the personal microenvironment. The conditioned air passes through the personal microenvironment where it picks up body heat and then is forced back into the external ambient air again through openings in the personal microenvironment boundary. Body armor is an example of where an open system cooling device as just described may be employed because the air on the inside of the body armor is only partially isolated from the air on the outside. That is, the ambient air and the air located between the body armor and the body are fluidly connected with each other at the openings in the body armor such as where the wearer's limbs, torso and neck may pass. Alternatively, the heat transfer fluid may be a fluid other than ambient air, but may be otherwise exhausted to the ambient environment in the same manner as just described. If the heat transfer fluid is a liquid, such as ethylene glycol or propylene glycol, then the heat transfer fluid would typically be circulated in a closed loop (e.g., through a cooling vest such as available from MedEng, Inc.)

Optionally, fluid handling apparatus according to embodiments of the present invention (e.g., the fluid handling apparatus 100) may be provided with one or more filters to filter contaminants or the like from the heat transfer fluid stream. For example, one or more filters may be mounted in the flow passage 144.

In some applications for cooling a personal microenvironment, it may be desirable to provide a distribution garment in accordance with embodiments of the present invention to distribute the conditioned heat transfer fluid (e.g., air) over portions of the body. According to some embodiments, the distribution garment is worn adjacent to the body, preferably under clothing. An outlet duct carries the conditioned air from the outlet of the air handler to a manifold of the distribution garment. The conditioned air flows through the manifold where it is then subdivided into multiple smaller streams of air, each of which flow through one of several separate distribution ducts that are formed into the garment. The conditioned air is approximately uniformly released through the inner surface of the garment against the surface of the body along the length of each of the distribution ducts. As this conditioned heat transfer fluid is released against the surface of the body it removes heat from the body in the form of both sensible heat and latent heat (e.g., in perspiration). This heat transfer fluid stream therefore becomes warmer and of high humidity. The continual flow of additional conditioned heat transfer fluid forces this warmer, more humid heat transfer fluid to flow toward openings in the clothing, body armor, etc., back into the external environment (in an open loop system) or the fluid handling apparatus (in a closed loop system).

According to some embodiments, a distribution garment as described (e.g., in the form of a vest) is generally shaped to fit in close proximity to, and preferably in contact with, the parts of the body to be cooled. The garment is fabricated from two layers of material: an inner layer and an outer layer. The outer layer of material is designed to be relatively impermeable to air flow. This can be accomplished by selecting a fabric which has a tight weave (such as Dacron sail cloth or parachute cloth) or which is coated with a sealant coating. The inner layer of fabric is designed to be relatively permeable to the flow of air. This permeable layer may be constructed from a relatively loose weave fiber such as a low thread count cotton. Alternatively, the inner layer could be made from relatively impermeable material (such as Dacron) that has small perforations placed at the locations where it is desired to have airflow onto the body. Moreover, the inner layer could be formed from a combination of impermeable and permeable materials where the permeable materials are located at the locations where it is desired do to have airflow onto the body. The manifold and air distribution ducts within the cooling garment can be created by selectively bonding the inner fabric layer to the outer fabric layer. The bonding of the two fabric layers may be accomplished by stitching or adhesive bonding, for example. The selective bonding of the two fabric layers creates multiple, separate but contiguous channels or ducts which can carry flowing air to the various parts of the body. The channels are created between the bonded and unbonded areas of the garment. The ducts may be arranged so that there is an evenly or selectively distributed flow of the conditioned air over the surfaces of the body where it can pick up heat and moisture. This warm, moist air is then discharged to the external environment or the fluid handling apparatus as described above. Optionally, the duct spaces may be filled with a material that is permeable to gas flow but which is rigid enough to prevent closure of the duct space (e.g., due to compressive forces between the body and body armor). Open cell foam, for example, could be inserted into the manifold and duct spaces.

While the present invention has been described with respect to personal environments, it is also contemplated that fluid handling apparatus and systems in accordance with further embodiments may be used to provide a heat transfer fluid flow through other microenvironments, such as an electronic device microenvironment. Such an electronic device microenvironment may include an electronic device that generates heat and is disposed in a chamber of a housing, wherein the fluid handling apparatus provides a flow of conditioned heat transfer fluid through the chamber.

Figure 4:
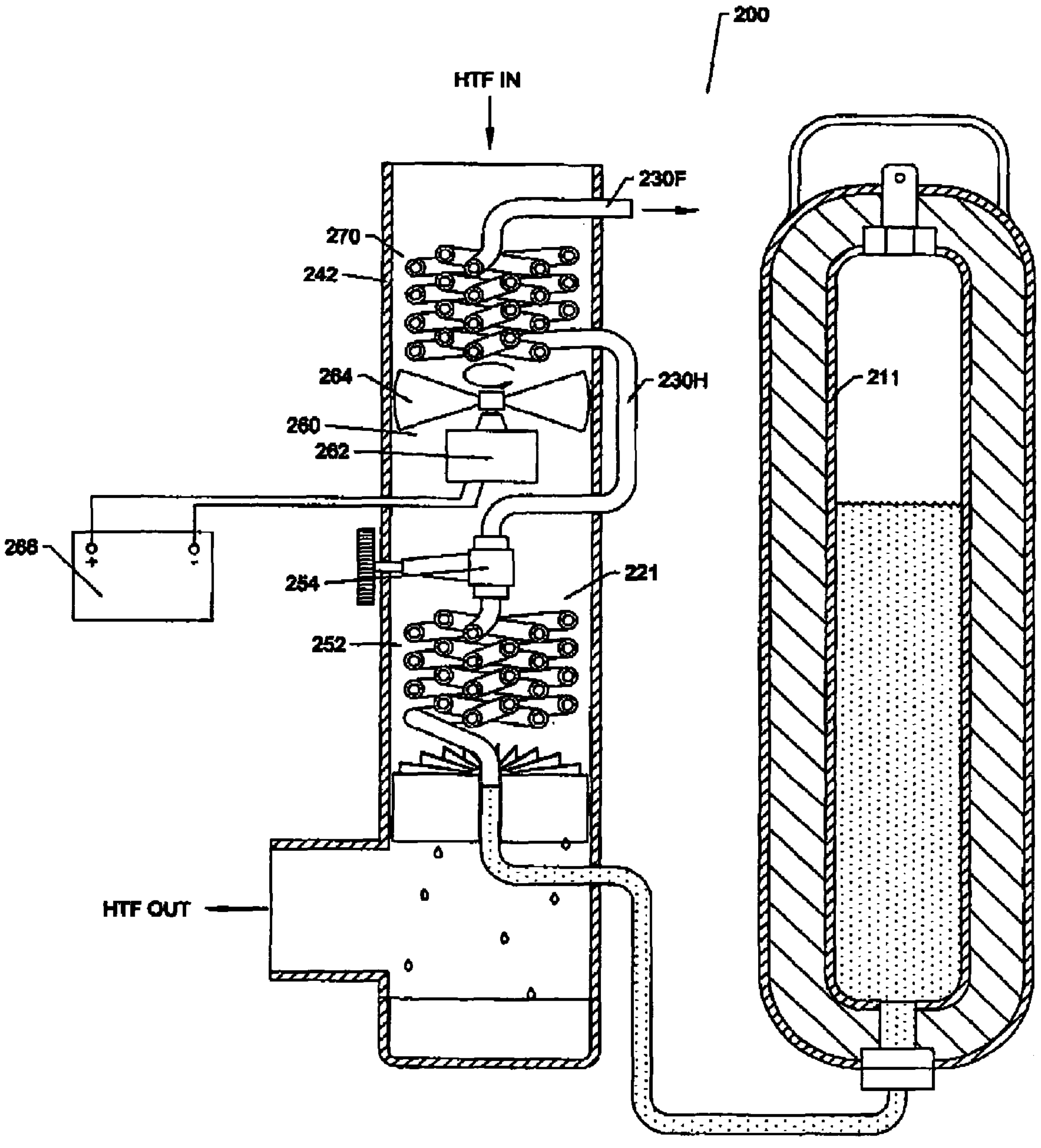
FIG. 4 is an enlarged, fragmentary, cross-sectional view of a fluid handling apparatus in accordance with further embodiments of the present invention.

With reference to FIG. 4, a fluid handling apparatus 200 according to further embodiments of the present invention is shown therein. The apparatus 200 may be used in place of the fluid handling apparatus 100. In the illustrated embodiment, the apparatus 200 corresponds to and may be operated in the same manner as discussed with regard to the apparatus 100, except as follows.

In the apparatus 200, the flow of the heat transfer fluid is moved using an electrically driven pump 260 in place of the gas driven pump 160. The PCM flows through a PCM handler subassembly 221 to cool the heat transfer fluid flowing through the housing 242. The PCM handler subassembly 221 may be constructed in similar manner to the PCM subassembly 121 except that a conduit 230H connects the valve 254 to the scavenger 270 without an intervening gas driven pump.

The electrically driven pump 260 includes an electric motor 262 and a fan blade 264. The electric motor 262 may be of any suitable type. According to some embodiments, the electric motor 262 is a direct current type motor and is constructed to have a drive voltage of between 6 and 24 volts, according to some embodiments about 9 volts, and a drive current of between abut 0.5 amps and 10 amps, according to some embodiments about 2 amps. A power supply 266 is operatively connected to the motor 262 to supply a desired voltage and current to the motor 262. According to some embodiments, the power supply 266 is a battery that is portable with the microenvironment. According to some embodiments, the battery 266 is mounted on the suit 20. According to some embodiments, the battery 266 has a supply voltage of about 9 volts, a capacity of at least about 2 amp-hours, and is a nickel metal hydride battery.

One or more of the components of the PCM handler subassembly 221 may be modified or supplemented to provide greater resistance to the flow of the PCM (e.g., $CO_2$) therethrough in order to compensate for the absence of the gas driven pump and provide the desired pressure drop between the storage vessel 211 and the exhaust 230F. This may be accomplished by reducing the inner diameter of the heat exchanger tubing of the superheater 252 and/or the scavenger 270 to about 0.050" and/or by selective operation of the valve 254.

As in the apparatus 100, the PCM is vented (e.g., into the external ambient environment and/or into the heat transfer fluid stream) after flowing through the PCM handler subsystem 221. As described before, it may be advantageous to omit the scavenger heat exchanger 270 altogether and to discharge the PCM directly into the environment or into the heat transfer fluid stream after the PCM exits the valve 254.

According to further embodiments, the electrically driven pump 260 may be replaced with another type of pump. For example, a gas driven pump (with drive gas supplied by a source other than the PCM handler subassembly 221), a hydraulically driven pump, etc. As illustrated in FIG. 4, the fan blade 264 is of the axial type, but could also be of the radial type such as are referred to as a blower (when the fluid is a gas) or an impeller (when the fluid is a liquid).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

What is claimed is:

1. A microenvironment system for use with a heat transfer fluid, the microenvironment system comprising:

a) a microenvironment structure defining a flow passage to receive a flow of the heat transfer fluid therethrough, wherein the heat transfer fluid is a gas; and b) a fluid handling apparatus adapted to provide the flow of the heat transfer fluid through the flow passage, the fluid handling apparatus including:
an insulated storage vessel;
a supply of a phase change material (PCM) stored in the storage vessel and convertible from a liquid phase to a gas phase to provide a pressurized drive gas, wherein the supply of the PCM includes liquid $CO_2$;
an evaporator downstream of and external to the storage vessel and adapted to boil the supply of the PCM from the liquid phase to the gas phase to form the pressurized drive gas; and
a gas driven pump operable to force the flow of the heat transfer fluid through the flow passage, wherein the gas driven pump includes a gas driven motor and a fan blade;
wherein:
the fluid handling apparatus is configured to supply the pressurized drive gas from the evaporator to the gas driven motor to drive the gas driven motor using the pressurized drive gas; and
the gas driven motor is coupled to the fan blade to rotate the fan blade to force the flow of the heat transfer fluid through the flow passage and across the evaporator to cool and remove humidity from the heat transfer fluid.

2. The system of claim 1 wherein the evaporator is adapted to transfer heat from the heat transfer fluid to the PCM.

3. The system of claim 2 wherein the PCM flows through the evaporator.

4. The system of claim 1 wherein the fluid handling apparatus further includes a superheater adapted to superheat the pressurized drive gas prior to introduction of the pressurized drive gas into the gas driven pump.

5. The system of claim 1 wherein the microenvironment is a personal microenvironment.

6. The system of claim 5 wherein the personal microenvironment includes a protective garment.

7. The system of claim 1 wherein the microenvironment is an electronic device microenvironment.

8. The system of claim 1 wherein the heat transfer fluid is air.

9. The system of claim 1 wherein the microenvironment structure and the fluid handling apparatus form a continuous closed loop flow path for the heat transfer fluid.

10. The system of claim 1 wherein the microenvironment structure and the fluid handling apparatus form an open loop flow path for the heat transfer fluid.

11. The system of claim 1 wherein the fluid handling apparatus further includes a superheater downstream of the evaporator and adapted to superheat the cooling gas using heat transferred from the heat transfer fluid.

12. A microenvironment system for use with a heat transfer fluid, the microenvironment system comprising:
a) a microenvironment structure defining a flow passage to receive a flow of the heat transfer fluid therethrough; and
b) a fluid handling apparatus adapted to provide the flow of the heat transfer fluid through the flow passage, the fluid handling apparatus including:
a gas driven pump operable to force the flow of the heat transfer fluid through the flow passage;
a supply of a phase change material (PCM) convertible from a liquid phase to a gas phase to provide a pressurized drive gas;
an insulated storage vessel, wherein the supply of the PCM is stored in the storage vessel at a pressure in the range of from about 140 to 160 psia and a temperature of between about −58 and 65° F.;
a bleed valve to maintain the pressure in the storage vessel at a desired level;
an evaporator downstream of and external to the storage vessel and adapted to boil the supply of the PCM from the liquid phase to the gas phase to form the pressurized drive gas; and
a superheater downstream of the evaporator and adapted to superheat the pressurized drive gas to a temperature of between about 40 and 80° F. prior to introduction of the pressurized drive gas into the gas driven pump;
wherein:
the fluid handling apparatus is configured to drive the gas driven pump using the pressurized drive gas from the supply of the PCM;
the heat transfer fluid is a gas;
the supply of the PCM includes liquid $CO_2$;
the gas driven pump includes a gas driven motor and a fan blade;
the fluid handling apparatus is configured to supply the superheated pressurized drive gas to the gas driven motor to drive the gas driven motor; and
the gas driven motor is coupled to the fan blade to rotate the fan blade to force the flow of the heat transfer fluid through the flow passage and across the evaporator and the superheater to cool and remove humidity from the heat transfer fluid.

13. The system of claim 12 wherein
the PCM flows through the evaporator.

14. A method for providing a flow of a heat transfer fluid through a flow passage of a microenvironment structure, the method comprising:
providing a supply of a phase change material (PCM) stored in a storage vessel and convertible from a liquid phase to a gas phase to provide a pressurized drive gas, wherein the supply of the PCM includes liquid $CO_2$;
directing the PCM in the liquid phase from the storage vessel to an evaporator downstream of and external to the storage vessel, where the supply of the PCM is boiled from the liquid phase to the gas phase to form the pressurized drive gas; and
supplying the pressurized drive gas from the evaporator to a gas driven motor of a gas driven pump to drive the gas driven motor using the pressurized drive gas, wherein the gas driven motor is coupled to a fan blade of the gas driven pump and rotates the fan blade to force the flow of the heat transfer fluid through the flow passage and across the evaporator to cool and remove humidity from the heat transfer fluid;
wherein the heat transfer fluid is a gas.

* * * * *